(12) United States Patent
Thompson

(10) Patent No.: US 8,623,009 B2
(45) Date of Patent: Jan. 7, 2014

(54) ENDOSCOPIC GASTRIC BYPASS DEFECT REPAIR

(75) Inventor: Christopher C. Thompson, Needham, MA (US)

(73) Assignees: The Brigham and Women's Hospital, Inc., Boston, MA (US); The General Hospital Corporation, Boston, MA (US)

( * ) Notice: Subject to any disclaimer, the term of this patent is extended or adjusted under 35 U.S.C. 154(b) by 1161 days.

(21) Appl. No.: 11/909,728

(22) PCT Filed: Apr. 5, 2006

(86) PCT No.: PCT/US2006/012680
§ 371 (c)(1),
(2), (4) Date: Jun. 9, 2010

(87) PCT Pub. No.: WO2006/108050
PCT Pub. Date: Oct. 12, 2006

(65) Prior Publication Data
US 2010/0268022 A1    Oct. 21, 2010

Related U.S. Application Data

(60) Provisional application No. 60/668,822, filed on Apr. 5, 2005, provisional application No. 60/694,617, filed on Jun. 27, 2005.

(51) Int. Cl.
*A61B 18/04* (2006.01)

(52) U.S. Cl.
USPC .......................................................... 606/41

(58) Field of Classification Search
USPC ............................................. 606/27, 34, 41
See application file for complete search history.

(56) References Cited

U.S. PATENT DOCUMENTS

| 3,604,425 | A | * | 9/1971 | Le Roy | 606/158 |
|---|---|---|---|---|---|
| 4,928,603 | A | * | 5/1990 | Rose et al. | 106/124.1 |
| 5,127,421 | A | * | 7/1992 | Bush et al. | 607/130 |
| 5,759,185 | A |   | 6/1998 | Grinberg |   |

(Continued)

FOREIGN PATENT DOCUMENTS

| WO | WO 95/29626 | 11/1995 |
|---|---|---|
| WO | WO 99/45847 | 9/1999 |
| WO | 2004/021894 | 3/2004 |
| WO | 2005/037152 | 4/2005 |

OTHER PUBLICATIONS

EP Search Report dated Mar. 22, 2010 for corresponding EP Application No. 06740569.6 filed on Apr. 5, 2006.

(Continued)

*Primary Examiner* — Michael Peffley
*Assistant Examiner* — Daniel Fowler
(74) *Attorney, Agent, or Firm* — Fish & Richardson P.C.

(57) ABSTRACT

The invention relates to systems or kits and methods for repairing defects in gastric bypass operations, e.g., methods of closing intragastric fistulas (18, 20) and dilated gastrojejunal anastomoses. In various embodiments, an endoscopic suturing device (23) is inserted through a patient's mouth, down through the esophagus, and positioned in the region of the defect, e.g., fistula. Adjacent tissue is then acquired, e.g., by vacuum, and one or more stitches are placed through the tissue and tightened to at least partially close the fistula, forming a suture line. One or more reinforcing clips (30) and sealant (32) can be endoscopically applied to the suture line.

14 Claims, 21 Drawing Sheets

(56) References Cited

U.S. PATENT DOCUMENTS

| | | | |
|---|---|---|---|
| 5,844,087 A * | 12/1998 | Zimmerman et al. | 530/381 |
| 6,156,028 A * | 12/2000 | Prescott | 606/2 |
| 2002/0183768 A1 | 12/2002 | Deem et al. | |
| 2003/0191476 A1 | 10/2003 | Smit | |
| 2003/0208209 A1 * | 11/2003 | Gambale et al. | 606/144 |
| 2004/0034371 A1 | 2/2004 | Lehman et al. | |
| 2005/0021085 A1 | 1/2005 | Abrams et al. | |
| 2005/0055040 A1 | 3/2005 | Tal | |

OTHER PUBLICATIONS

EP Office Action for Application No. 06 740 569.6, dated Dec. 8, 2011, 4 pages.

International Search Report and Written Opinion of the International Searching Authority, mailed Mar. 27, 2007.

Thompson et al., "Peroral Endoscopic Repair of Staple-Line Dehiscence in roux-en-Y Gastric Bypass: A Less Invasive Approach," Gastroenterology, 126 (4, Supplement 2):A-810 (2004).

* cited by examiner

ENDOSCOPIC GASTRIC BYPASS DEFECT REPAIR

CROSS-REFERENCE TO RELATED APPLICATIONS

This application is a US national stage entry under 35 USC 371 of PCT/US2006/012680 filed on Apr. 5, 2006, which claims the benefit of the priority dates of U.S. Application Ser. Nos. 60/668,822, filed on Apr. 5, 2005, and 60/694,617, filed on Jun. 27, 2005, the contents of which are hereby incorporated by reference in their entirety.

TECHNICAL FIELD

This invention relates generally to endoscopic surgery, and more particularly to per-oral endoscopic surgery of the gastro-intestinal tract.

BACKGROUND

Bariatric procedures have become the fastest growing surgical procedures in the United States as a result of the continued rise of obesity rates and advances in laparoscopic techniques with improved surgical outcomes. It is estimated that over 100,000 bariatric operations were performed in 2003, and this number continues to grow. The Roux-en-Y gastric bypass (RNYGB) remains the most commonly performed bariatric surgical procedure in the United States and worldwide. RNYGB is the relative gold standard of such procedures, and accounts for about 85% of all bariatric procedures performed in the United States.

In an RNYGB procedure, stapling or sewing is employed to segment the stomach, creating a small gastric pouch (having a volume of about 15 to 30 ml) connected to the esophageal inflow, and a defunctionalized larger stomach portion, divided from the smaller pouch, but still connected to the intestinal tract to secrete digestive juices. A resected portion of the small intestine is then anastomosed to the gastric pouch, referred to as a gastrojejunostomy (GJ), bypassing the majority of the intestine, thereby reducing absorption of caloric intake.

While RNYGB has proven effective in achieving short-term weight loss, it is not a cure for obesity. Maximal weight loss is seen at roughly 1½ to 2 years (post-procedure) and this weight loss approximates 65 to 80% excess weight. What happens after this time is some degree of weight re-gain from years 2 to 10, but the reasons are not entirely clear. However, one factor thought to contribute to the long term failure of RNYGB for achieving sustained weight loss is the formation of intragastric fistulas, where small holes develop between the gastric pouch and the defunctionalized stomach as a result of staple line dehiscence. The staple line fistulas allow food from the gastric pouch to enter the previously defunctionalized portion of the stomach, facilitating an increased volume of oral food intake. The fistulas also allow acidic secretions to pass from the defunctionalized portion of the stomach to the gastric pouch, potentially causing ulcerations.

Other possible causes for the long-term weight gain are dietary non-compliance, dilated pouches, and dilated gastrojejunal anastomoses, the latter leading to less distension of the pouch with a solid meal, and a corresponding decreased satiety response. Surgical interventions have been used to correct the physical defects of gastric bypass, such as staple line fistulas and dilated gastrojejunal anastomoses, but such repeat surgical interventions cause a significant increase in mortality and morbidity.

SUMMARY

The invention is based, in part, on the discovery that various defects of gastric bypass operations, such as intragastric fistulas and dilated gastrojejunal anastomoses, can be repaired effectively, safely, and with far fewer complications and at a lower cost than open, invasive abdominal surgical procedures, by using a per-oral endoscopic approach, which avoids the need for an abdominal incision.

In one aspect, the invention features systems for per-oral endoscopic repair of a gastric bypass defect, the system including an endoscopic tissue apposition device (e.g., a suturing device or stapling device that can include a thermal ablation device, for example); a thermal ablation device (e.g., an ablation catheter, argon plasma coagulator, or heat probe) configured to damage a tissue portion adjacent the defect; and a mechanical abrader (e.g., cytology brush) configured to remove the damaged tissue portions adjacent the defect; packaged for use in a method of per-orally reducing a dilated gastrojejunal anastomosis. In various embodiments, the system can include a biocompatible sealant (e.g, fibrin glue or cyanoacrylate) to protect and isolate the damaged tissue and/or a plurality of endoscopic clips such as hemostatic clips.

In another aspect, the invention features methods of repairing defects resulting from gastric bypass surgeries, such as RNYGB. The methods include damaging tissue portions adjacent to the defect; removing at least some of the damaged tissue portions adjacent to the defect; perorally and endoscopically advancing a suturing device (e.g., any device that is used to insert a suture, staple, clip, or other tissue holding device) into a patient (through the mouth and esophagus) adjacent to the defect; gathering together or holding a first fold of tissue along a rim of the defect; operating the suturing device to advance a first tissue holding device through or into the first fold of tissue; gathering together or holding a second fold of tissue along the rim of the defect, adjacent to the first fold of tissue; operating the suturing device to advance a second tissue holding device through or into the second fold of tissue; and bringing together the first and second folds of tissue to at least partially close the defect, e.g., by tightening first and second suture materials to form a suture line, or by bringing together the tissue holding devices, such as staples or clips, e.g., using suture material.

In certain embodiments, the defect is a dilated gastrojejunal anastomosis. In other embodiments, the defect is a fistula resulting from staple line dehiscence.

In various embodiments of the new methods, vacuum pressure can be employed to gather portions or folds of tissue. Thermal ablation using, for example, heat probes or argon plasma coagulation, can be employed to damage tissue surrounding the fistulas as a means of engendering new tissue growth and adhesions. Mechanical abrading may be used to remove damaged tissue, such as with an endoscopic brush such as a cytology brush.

In certain embodiments of the new methods, endoscopically placed sutures can be interrupted or instead can be formed from a single continuous strand or thread of material. For example, purse string suture techniques can be employed. In various embodiments, the suture material can be tightened with a cinching device. The methods can include bringing two, three, or more folds of tissue together to reduce the defect. The method can include the application of a reinforcing clip to the first and second folds of tissue. In various embodiments, the reinforcing clips can be endoscopic reinforcing clips, such as endoscopic hemostatic clips.

Sealants can be applied to the suture material, staple, and/or clip, e.g., using a multi-lumen, open tip catheter inserted through the endoscope. The catheter can be a double-lumen catheter with the lumens communicating in the region of the open tip.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIG. 18A shows the results for the eight patients after a single repair, and FIG. 18B shows results of the same patients including those who had a second repair.

Like reference symbols in the various drawings indicate like elements.

DETAILED DESCRIPTION

While the techniques disclosed herein are described in the context of closing a fistula located between the gastric pouch and the defunctionalized portion of the stomach formed during Roux-en-y gastric bypass surgery, or reducing a gastrojejunal anastomosis, it is contemplated, and will be understood, that the these techniques are not limited to these uses, but can be used to close any hole, tear, or other defect identified in the gastro-intestinal tract. It is further contemplated that the techniques disclosed herein may be used in lieu of or in connection with, open or laparoscopic surgical methods where tissue manipulation and fixation are required.

In one aspect, the present invention provides methods for performing transoral (per-oral) endoscopic repair or revision of a staple line formed in a traditional Roux-En-Y gastric bypass surgery. Specifically, the present techniques can be used to address an intragastric fistula where a small hole develops between the gastric pouch and the defunctionalized portion of the stomach as a result of staple or suture line dehiscence.

Figure 1A:
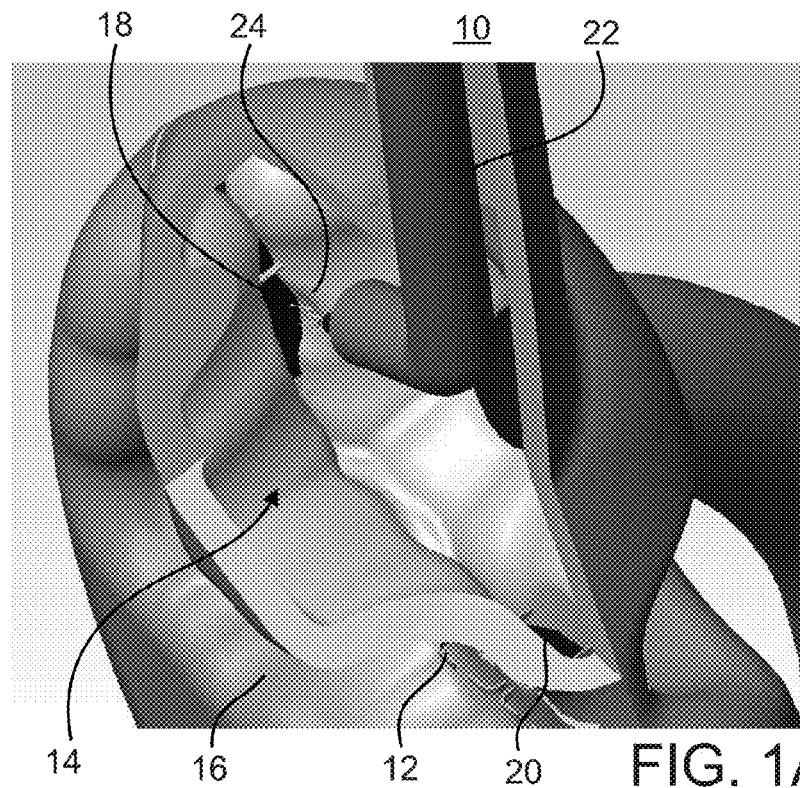
FIG. 1A is a schematic representation showing a partial cut-away view of a stomach modified by an open Roux-En-Y gastric bypass surgical procedure, in which tissue in the region of staple line fistulas is burned to stimulate tissue growth and promote healing.
Figure 1B:
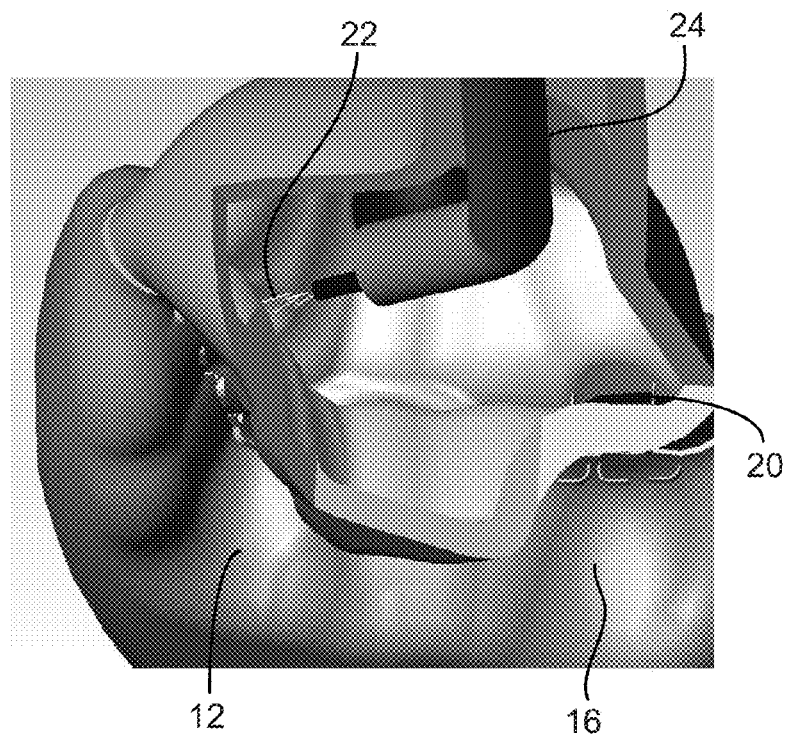
FIG. 1B is a schematic representation that shows another partial cut-away view of the modified stomach shown in FIG. 1A, in which tissue in the region of staple line fistulas is burned to stimulate tissue growth and promote healing.

FIGS. 1A and 1B show a partial cut-away view of a stomach 10 modified by an open Roux-En-Y gastric bypass surgical procedure. In the RNYGB procedure, a staple line 12 was introduced to divide the stomach, forming a small gastric pouch 14 and a larger defunctionalized stomach portion 16. The small gastric pouch serves to decrease the amount of food consumed by the patient before becoming satiated, thereby reducing the total caloric intake of the patient and ultimately resulting in weight loss.

Over time, however, fistulas 18, 20 may develop between the gastric pouch 14 and the defunctionalized portion of the stomach 16 as a result of staple or suture line dehiscence. The fistulas may result from a combination of factors such as wretching, dilation of the gastric pouch as a result of excessive food consumption, and tension placed on the gastric pouch by the anastomosed small intestine.

The fistulas 18, 20 allow food to pass from the gastric pouch 14 to the previously defunctionalized stomach 16, diminishing the effectiveness of the RNYGB procedure. Conversely, stomach acid from the larger defunctionalized stomach portion may pass into the gastric pouch and small intestine potentially causing ulceration of the small intestine.

In accordance with one illustrative embodiment of the invention, an endoscopic technique is employed to close a staple line fistula in the stomach. As further described herein, to repair the gastric staple line fistula, tissue portions surrounding the fistula are first traumatized to stimulated new tissue growth. After stripping away damaged tissue, the exposed tissue portions are sutured together, closing the fistula. The suture line may then be reinforced with endoscopically applied mechanical fasteners. Finally, the suture line may be covered with a sealant, which protects and isolates the repair from the environment, allowing the exposed, approximated tissues to grow together, bridging the fistula, thereby strengthening the repair. At the same time, the sealant inhibits traumatized tissue from adhering to other body tissues neighboring the region of the fistula repair.

More specifically, with continued reference to FIGS. 1A and 1B, a preferably flexible endoscope 22 is inserted through the patient's mouth, down through the esophagus and into the gastric pouch 14 near the region of the fistula 18. The fistula 18 is first thoroughly inspected, looking for signs of ischemia or adjacent vasculature.

Next, tissue surrounding the fistula is stimulated using one or more known methods such as, scraping, burning and thermally ablating. By stimulating new tissue growth, the approximated tissues eventually will grow together, strengthening the repair. In one embodiment, an argon plasma coagulator (APC) is employed to stimulate the tissue adjacent to the fistula. The APC, which is inserted through the lumen of the endoscope 22, is used to burn or ablate a region of tissue surrounding and defining the fistula 18. An attempt is made to apply argon plasma coagulation to both the gastric pouch side of the defect and the defunctionalized side. It will be appreciated that other known methods to stimulate new tissue growth may likewise be employed.

Figure 2A:
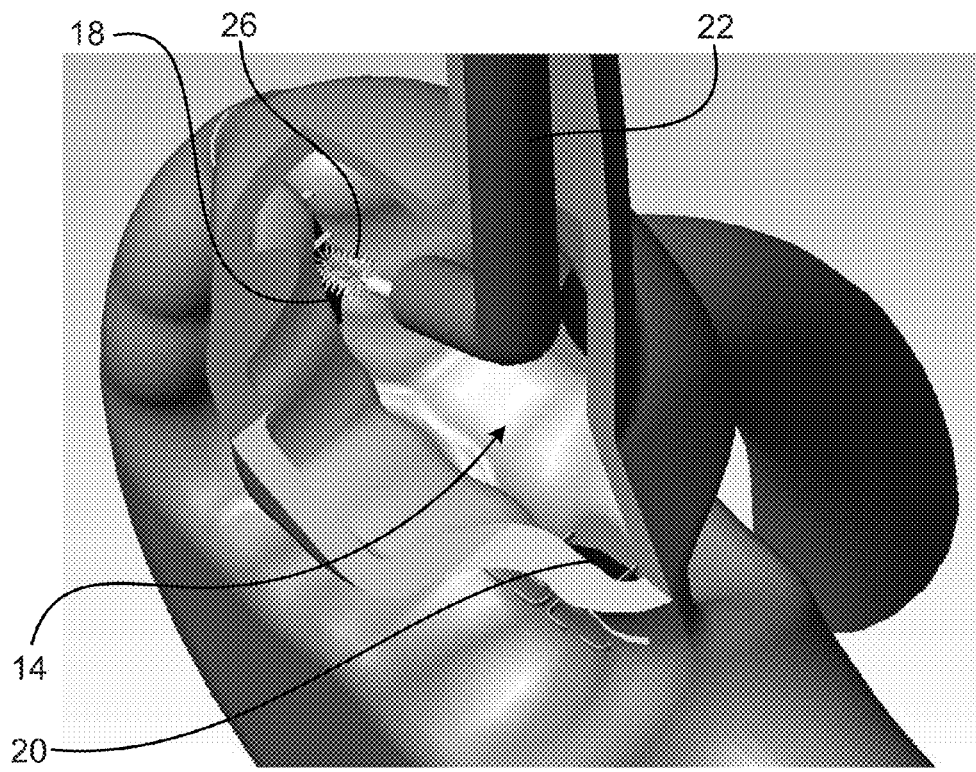
FIG. 2A is a schematic representation that shows a partial cut-away view of the modified stomach of FIGS. 1A and 1B, in which burned desiccated tissue is removed using an endoscopic brush.
Figure 2B:
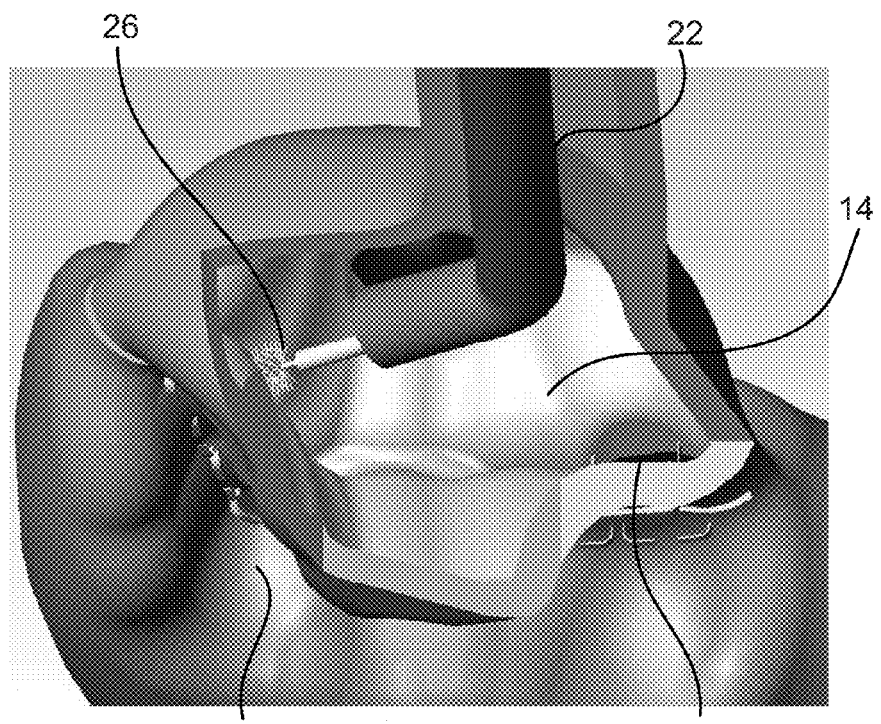
FIG. 2B is a schematic representation that shows another partial cut-away view of the modified stomach of FIGS. 1A and 1B, in which burned tissue is removed using an endoscopic brush.

After burning the tissue surrounding the fistula, the damaged tissue and mucosa is removed to expose the underlying tissue. Preferably, mechanical abrasion is used to remove the damaged tissue. In the illustrative embodiment, the damaged tissue and mucosa are endoscopically brushed away. As shown in FIGS. 2A and 2B, this procedure is performed by first removing the APC from the endoscope and replacing it with a conventional cytology brush 26. Using the cytology brush 26, the burned tissue is then excoriated and the mucosa stripped away.

Next, a guide wire (not shown) may be placed through the fistula 18 and into the defunctionalized stomach to mark the location of the fistula.

Figure 3A:
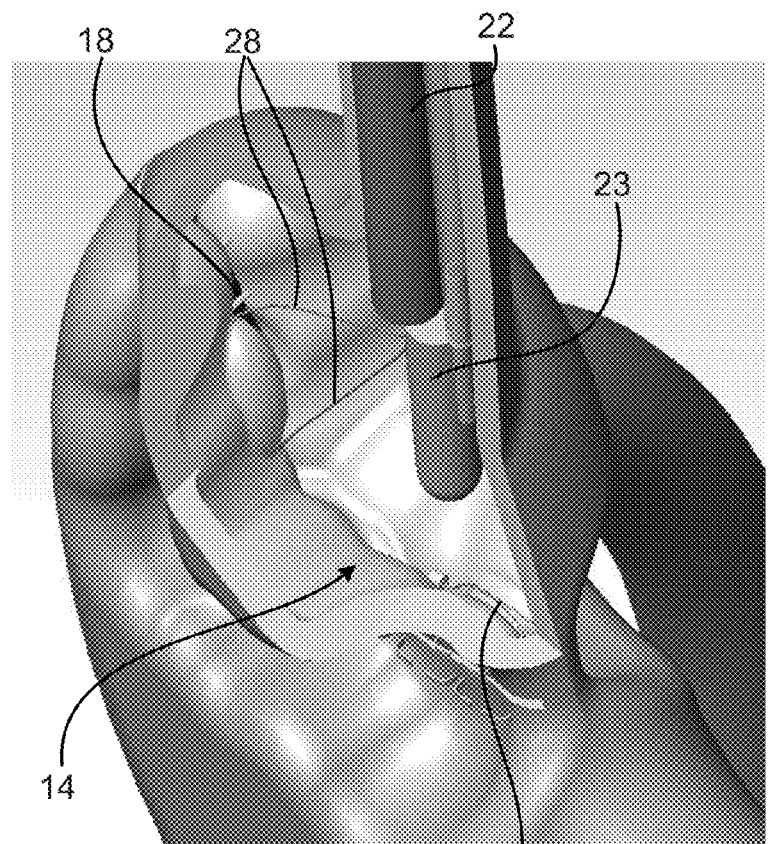
FIG. 3A is a schematic representation that shows a partial cut-away view of the modified stomach of FIGS. 1A and 1B, in which a first suture has been endoscopically placed near a fistula.
Figure 3B:
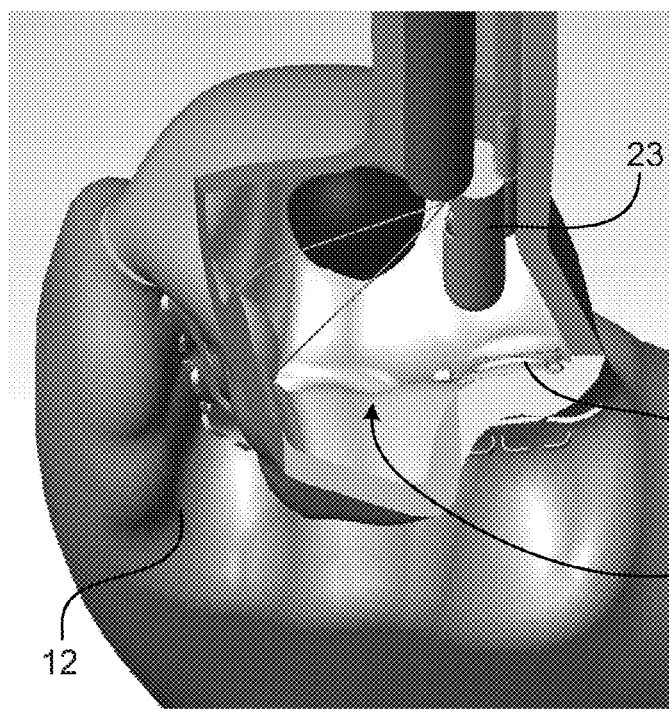
FIGS. 3B and 3C are schematic representations that show partial cut-away views of the modified stomach of FIGS. 1A and 1B, in which a first suture has been endoscopically placed near a fistula.

With reference to FIGS. 3A and 3B, after marking the location of the fistula 18, an endoscope 22 with an affixed suturing device 23 is placed through the mouth and into the gastric pouch 14. A useful device is the EndoCinch® suturing device available from C.R. Bard of Murray Hill, N.J. The EndoCinch® suturing device includes a generally cylindrically shaped capsule attachable to the distal end of an endoscope, preferably a flexible viewing endoscope. The capsule includes, in one embodiment, a body having an arc-shaped suction port into which portions of tissue can be captured. The suction port defines an opening to a vacuum chamber. The vacuum chamber is operated through a vacuum source line that can extend interiorly or exteriorly to the endoscope. Application of vacuum pressure causes tissue to be suctioned into the suction port and into the vacuum where suture material is advanced through the captured portions of tissue.

In the illustrative embodiment, shown in FIGS. 3A and 3B, the EndoCinch® suturing device is oriented such that the axis of the EndoCinch® suturing capsule is parallel to the fistula line. In this position, stitches 28 are placed in the tissue on opposite sides of, and in parallel with, the fistula 18. The stitches 28 are placed as interrupted stitches across from each other so that when the stitches are tied the defect is closed. Running stitches or a pursestring suturing technique may also be used. Several stitches are placed in this manner. The stitches are then tightened and individually tied, drawing the opposite edges of the fistula 18 together, closing and thereby providing a sutured defect 25.

Figure 3C:
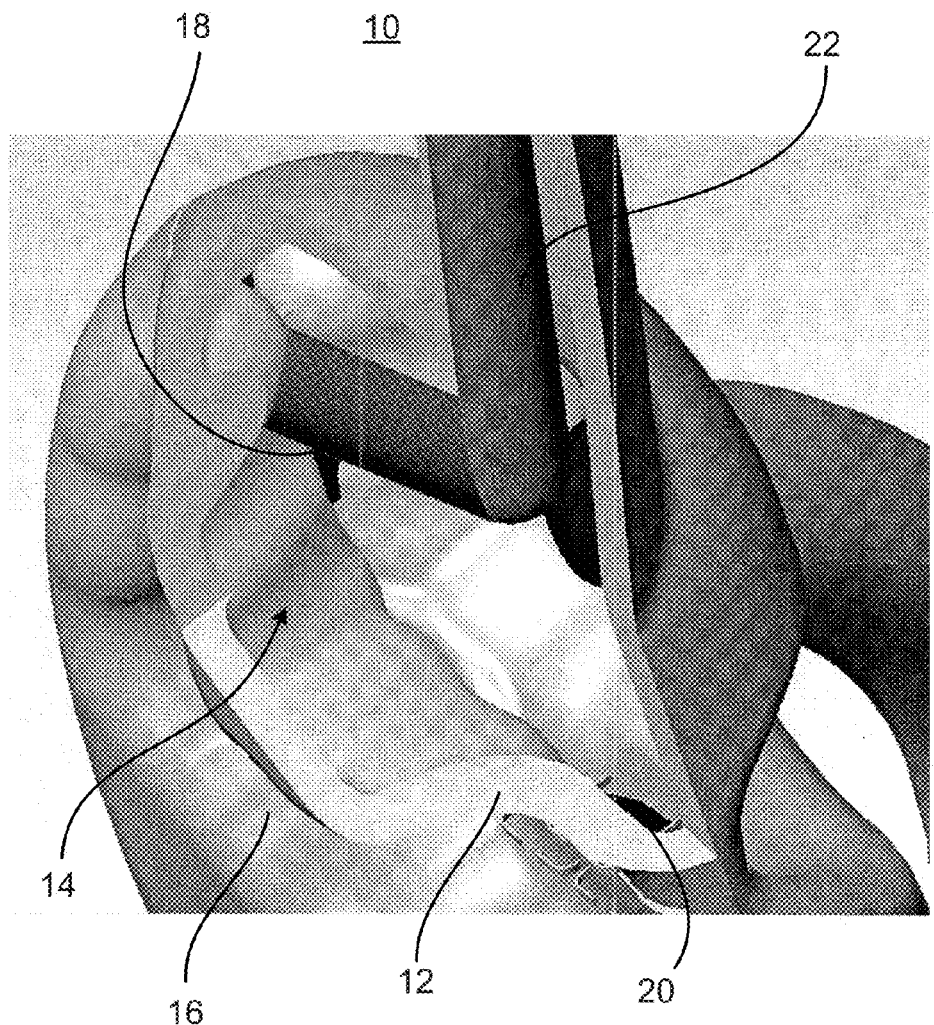

In another embodiment, shown in FIG. 3C, the EndoCinch® suturing device is positioned transverse to the fistula line such that end of the suturing device penetrates the fistula 18. Stitches are then placed on opposite sides of the fistula 18, in an orientation that is transverse to the fistula line. As with the previous embodiment, the stitches 28 are placed as interrupted stitches across from each other so that when the stitches are tied the defect is closed. Multiple stitches are placed around the defect in this manner. Alternatively, a single suture may be stitched in a continuous manner (also referred to as a purse-string stitch) to bridge and close the fistula. It will be appreciated that the number, location and orientation of stitches may vary depending on the size and location of the fistula.

Figure 4A:
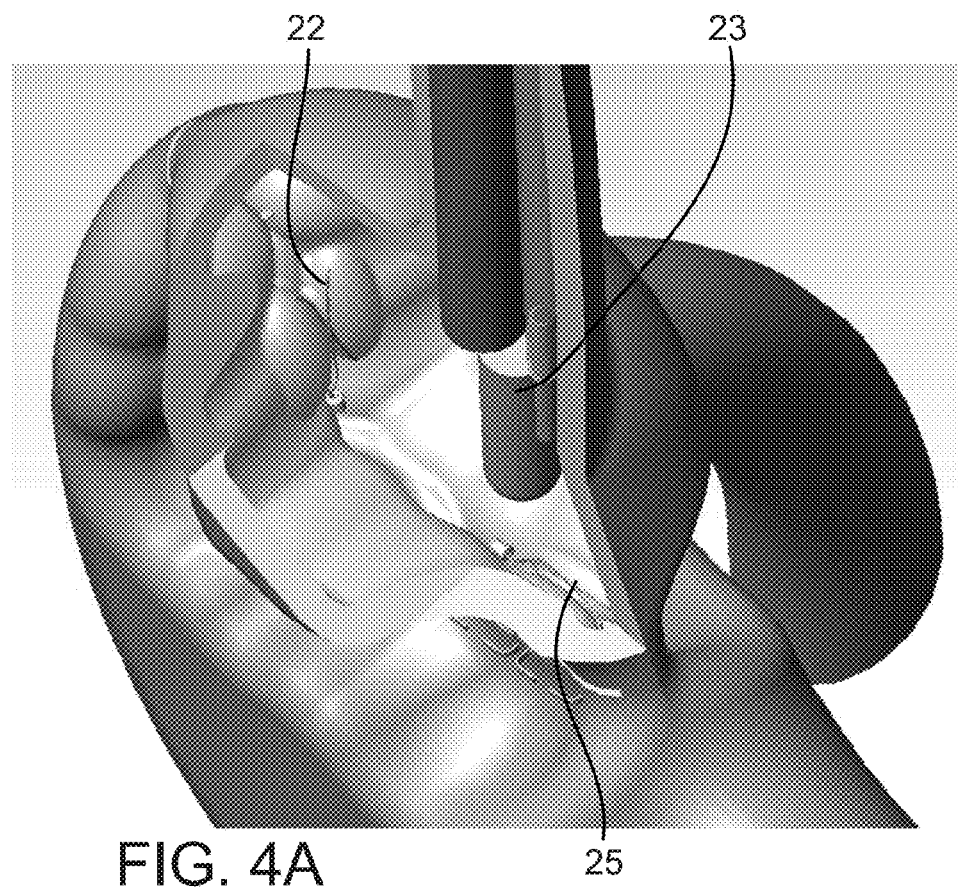
FIG. 4A is a schematic representation that shows a partial cut-away view of the modified stomach of FIGS. 1A and 1B, in which a second suture has been endoscopically placed opposite the first suture, the two sutures being tightened to close the fistula.
Figure 4B:
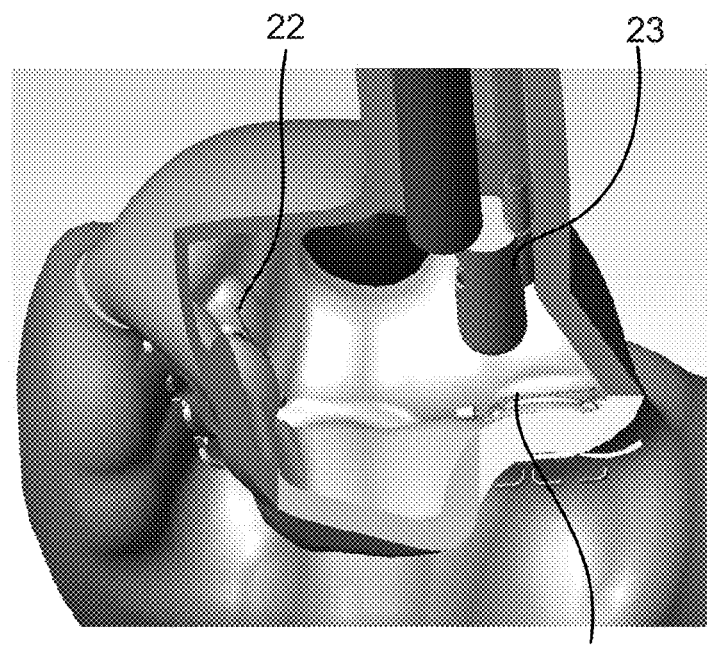
FIG. 4B is a schematic representation that shows another partial cut-away view of the modified stomach of FIGS. 1A and 1B, in which a second suture has been endoscopically placed opposite the first suture and cinched, the two sutures being tightened to close the fistula.

The stitches 28 are then tightened and individually tied, drawing the opposite edges of the fistula 18 together, closing the defect. An EndoCinch® clip system may be used to tighten and secure the stitches. Such a system is disclosed in U.S. patent application Ser. Nos. 10/220,379 and 10/275,534, the subject matter of which are hereby incorporated herein by reference in their entirety. FIGS. 4A and 4B show the modified stomach of FIGS. 1A and 1B, in which two sutures have been endoscopically placed on opposite sides of the fistulas, the two sutures being tightened to close the fistulas.

While the foregoing illustrative embodiment describes a technique for repairing a post gastric bypass fistula using the EndoCinch® endoscopic suturing device, it will be appreciated that any endoscopic suturing or stapling device, such as the Wilson-Cook ESD® or any other endoscopically deliverable tissue apposition device, can be employed for this technique.

In cases where the size or location of the fistula does not warrant suturing or stapling, other mechanical tissue apposition or fixation techniques, repair of the fistula may be accomplished by stimulating the tissue surrounding the fistula, stripping away damaged tissue portions and applying sealant to the region of the fistula to protect newly exposed tissues, allowing the tissues to grow together bridging the fistula.

Closure of the defects can be confirmed by filling the gastric pouch with water and compressing the defunctionalized stomach looking for air bubbles. If fluoroscopy is available, the gastric pouch may also be filled with contrast looking for persistent communication with the defunctionalized stomach.

Figure 5A:
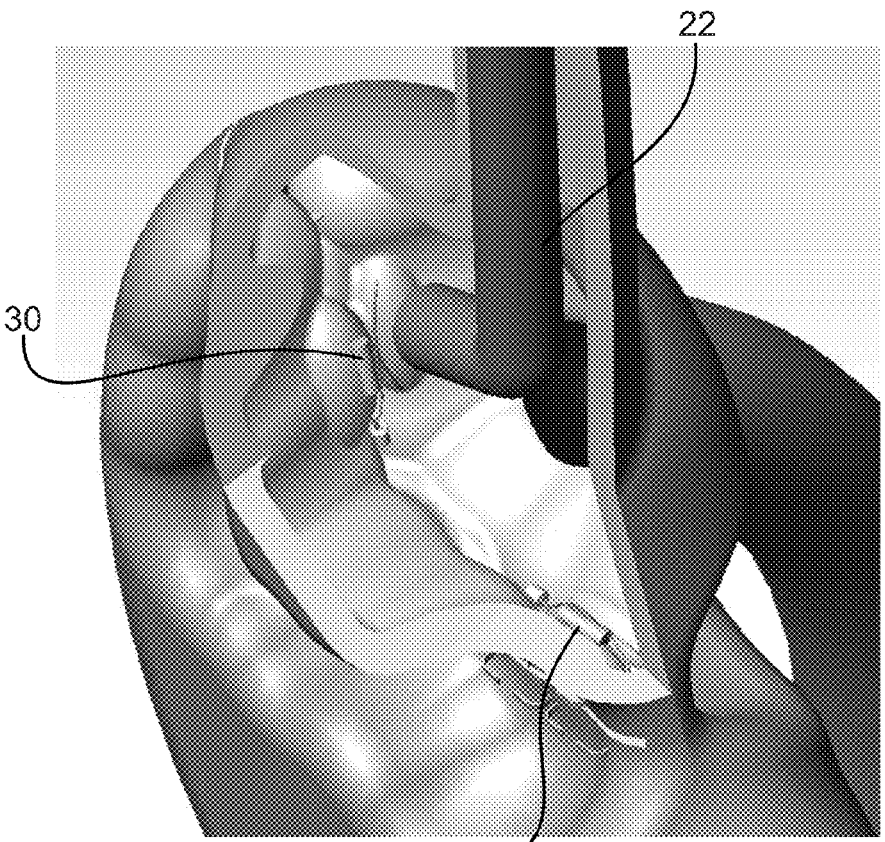
FIG. 5A is a schematic representation that shows a partial cutaway view of the modified stomach of FIGS. 4A and 4B, wherein a reinforcement clip is endoscopically applied to the area of closed fistula.
Figure 5B:
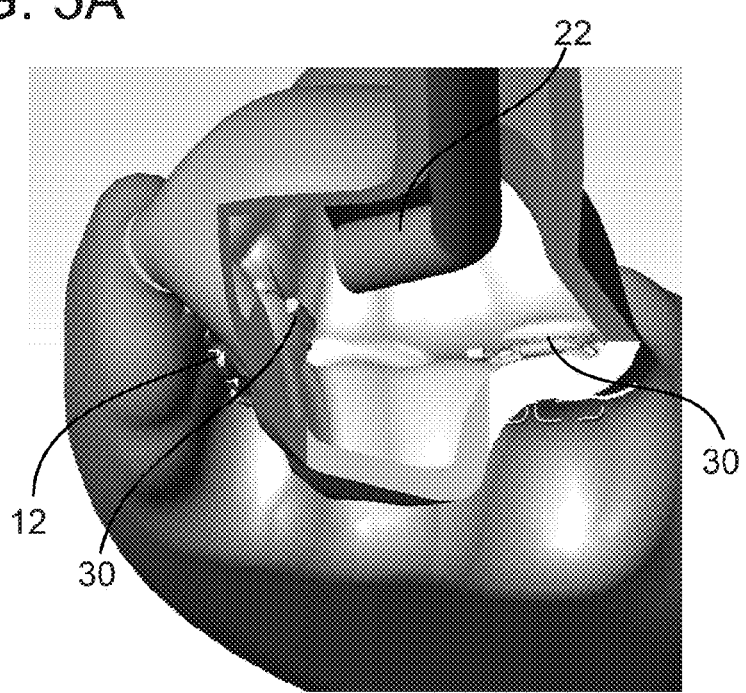
FIG. 5B is a schematic representation that shows another partial cut-away view of the modified stomach of FIGS. 4A and 4B, wherein a reinforcement clip is endoscopically applied to the area of closed fistula.

Referring to FIGS. 5A and 5B, the suture line may then be reinforced using endoscopically placed clips 30. Acceptable clips include endoscopic hemostatic clips such as the Olympus Quick Clip and the Microvasive Resolution Clip, or the Wilson Cook Tri-Clip. Alternatively, staples or clips can be used in place of the initial sutures.

Figure 6A:
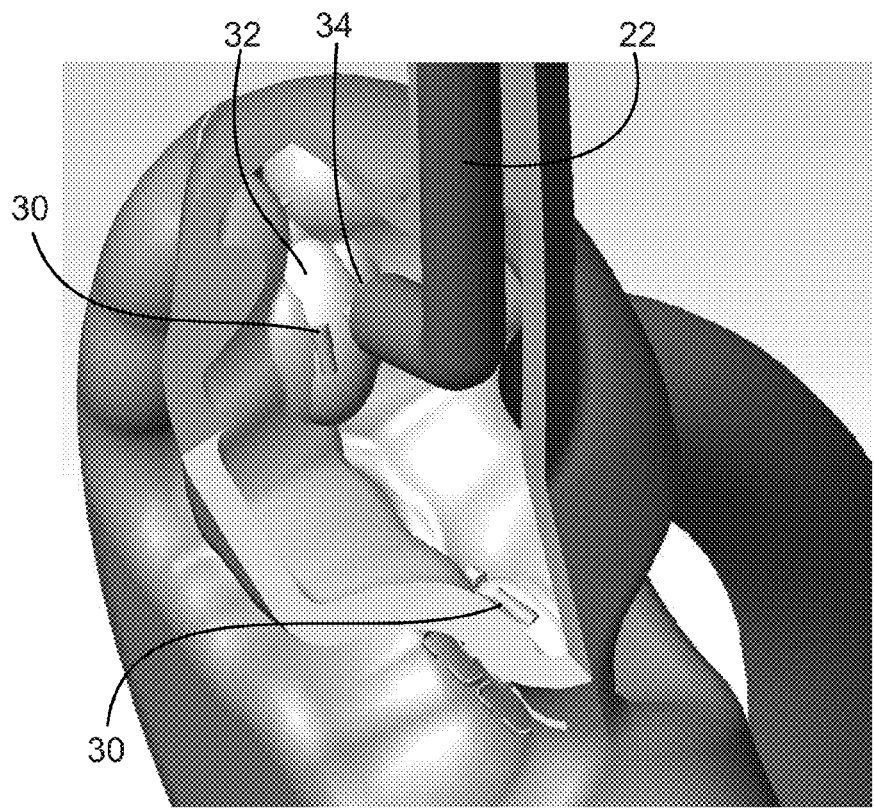
FIG. 6A is a schematic representation that shows a partial cut-away view of the modified stomach of FIGS. 5A and 5B, wherein a sealant is endoscopically applied to the area of the closed fistula.
Figure 6B:
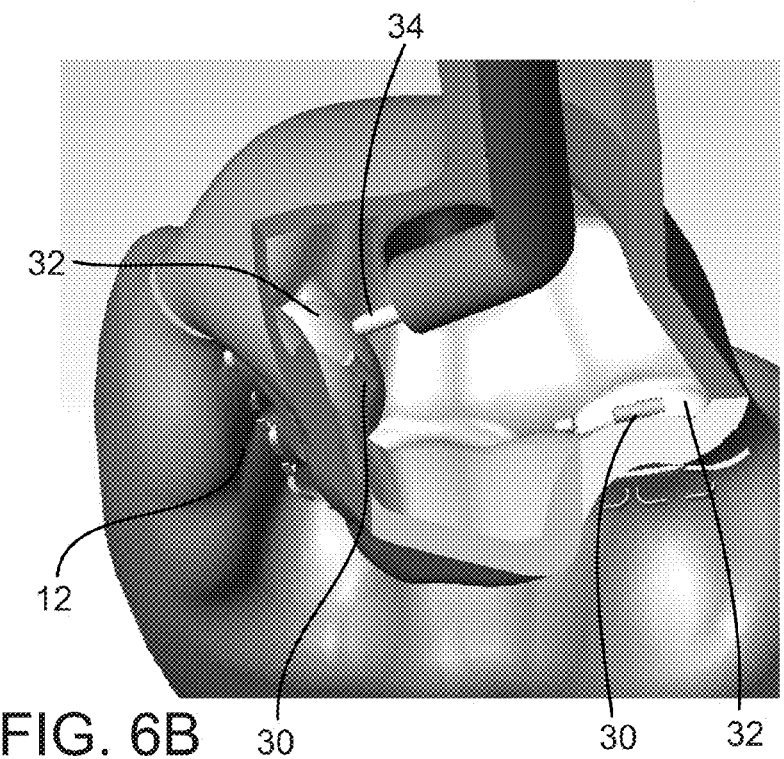
FIG. 6B is a schematic representation that shows another partial cut-away view of the modified stomach of FIGS. 5A and 5B, wherein a sealant is endoscopically applied to the area of the closed fistula.

As shown in FIGS. 6A and 6B, a sealant 32 may be applied to protect and isolate the traumatized tissue and reinforce the endoscopic clips and suture line. The term sealant as used herein is intended to include any biomaterial to promote healing, minimize inflammatory response and isolate traumatized tissue thereby inhibiting adhesions to other tissues neighboring the repair site. Sealants may include, for example, fibrin sealants, collagen-based sealants, and sealants comprising hygluronic acid or polymer hydrogels. One acceptable sealant is Tisseel®, a two-part fibrin sealant available from Baxter Corporation, of Glendale, Calif. In the case of a two-part sealant such as Tisseel®, the sealant may be applied using an endoscopically deliverable double-lumen catheter 34. The sealant is preferably applied in a sufficient quantity and distribution to thoroughly encapsulate the traumatized tissue, suture line and reinforcing clips. Typically, the sealant will remain intact for 2-3 weeks, after which the reinforcement clips will fall away and pass through the body.

Figure 7:
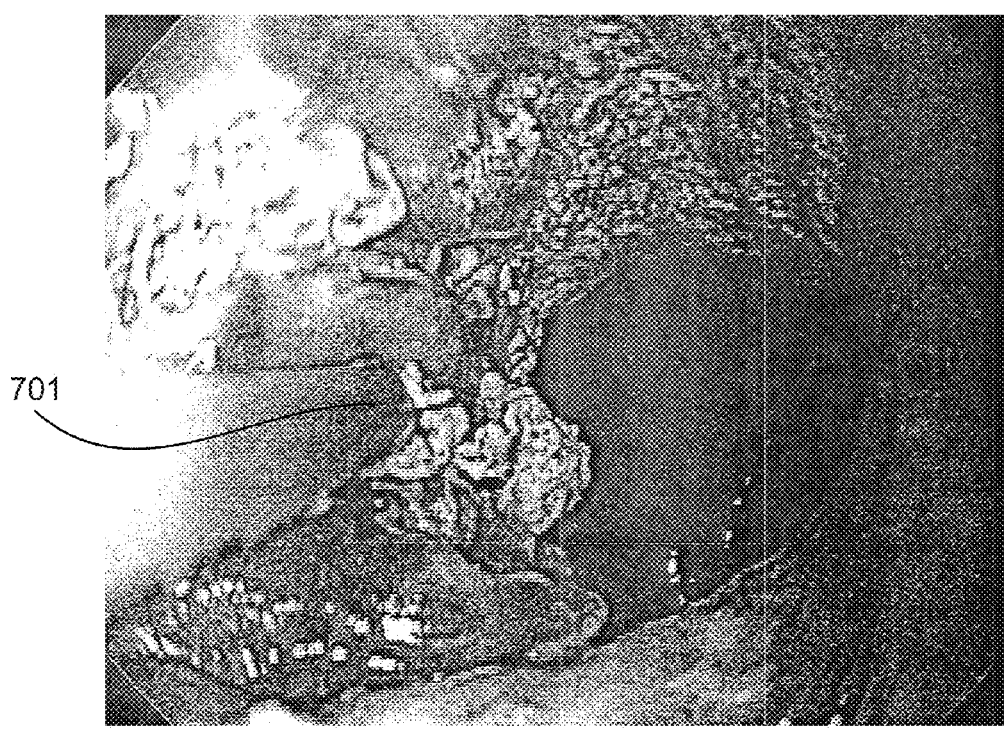
FIG. 7 is a representation of an endoscopic view of the thermal ablation using argon plasma coagulation of the mucosa at the rim of an anastomosis and surrounding tissue.
Figure 8:
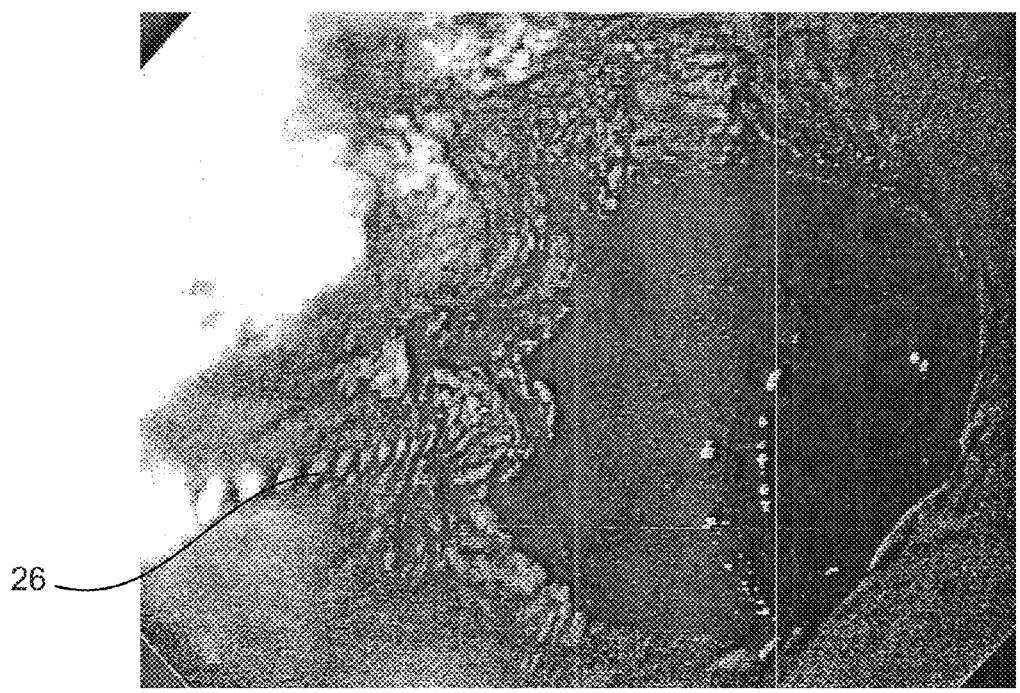
FIG. 8 is a representation of an endoscopic view of the removal of the thermally damaged mucosal tissue using a cytology brush.

The new methods can also be used in similar fashion to reduce the size of gastrojejunal anastomoses. In general, a dilated gastrojejunal anastomosis is first measured, e.g., with a 3 cm snare. As shown in FIG. 7, the mucosa is then damaged, e.g., ablated, e.g., thermally ablated, for example, using bi-cap cautery (argon plasma coagulation 701) at the rim of the anastomosis and surrounding tissue. The argon provides more uniform and consistent depth of ablation than other thermal methods. The mucosal tissue, or portions thereof, that has been thermally damaged is then stripped or excoriated (shown at 26), e.g., using a cytology brush, to promote better tissue healing (FIG. 8). Alternatively, excoriation can also be performed, without prior thermal damage.

Figure 11:
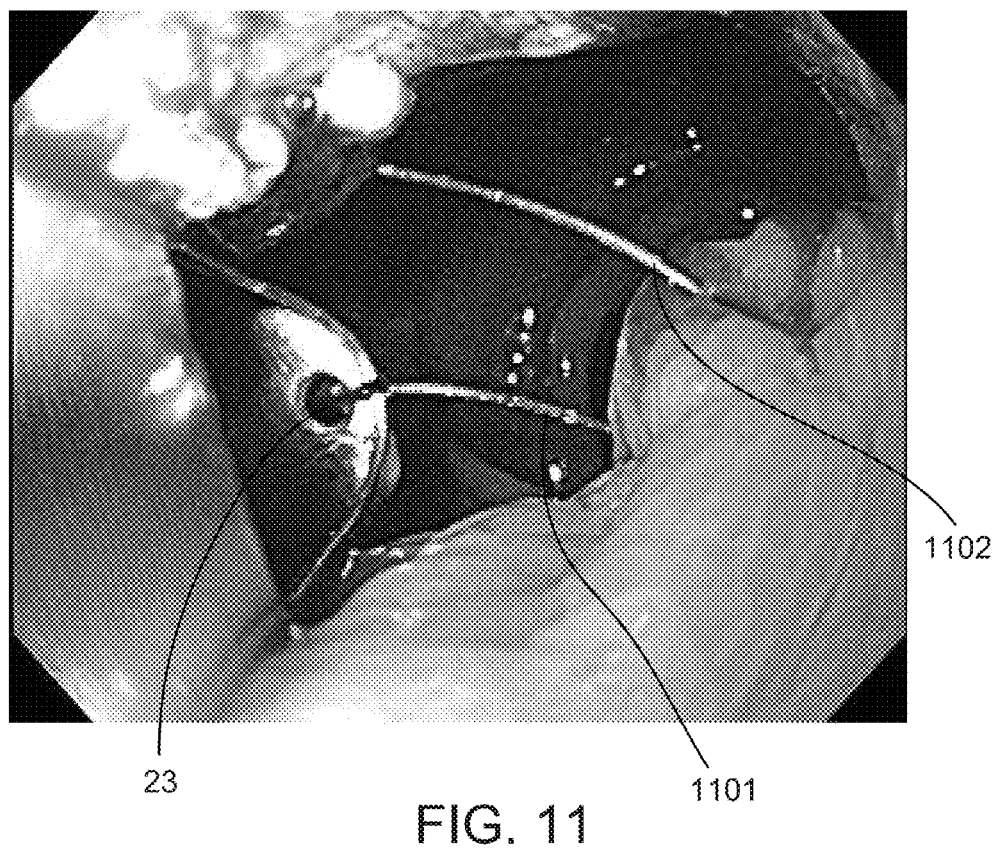
Figure 12:
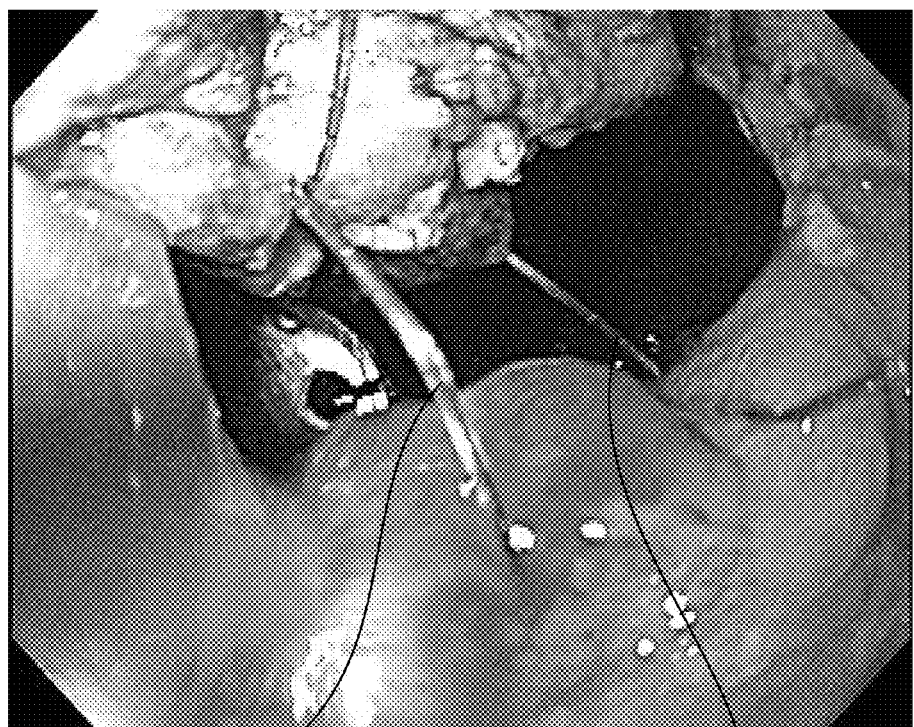
Figure 13:
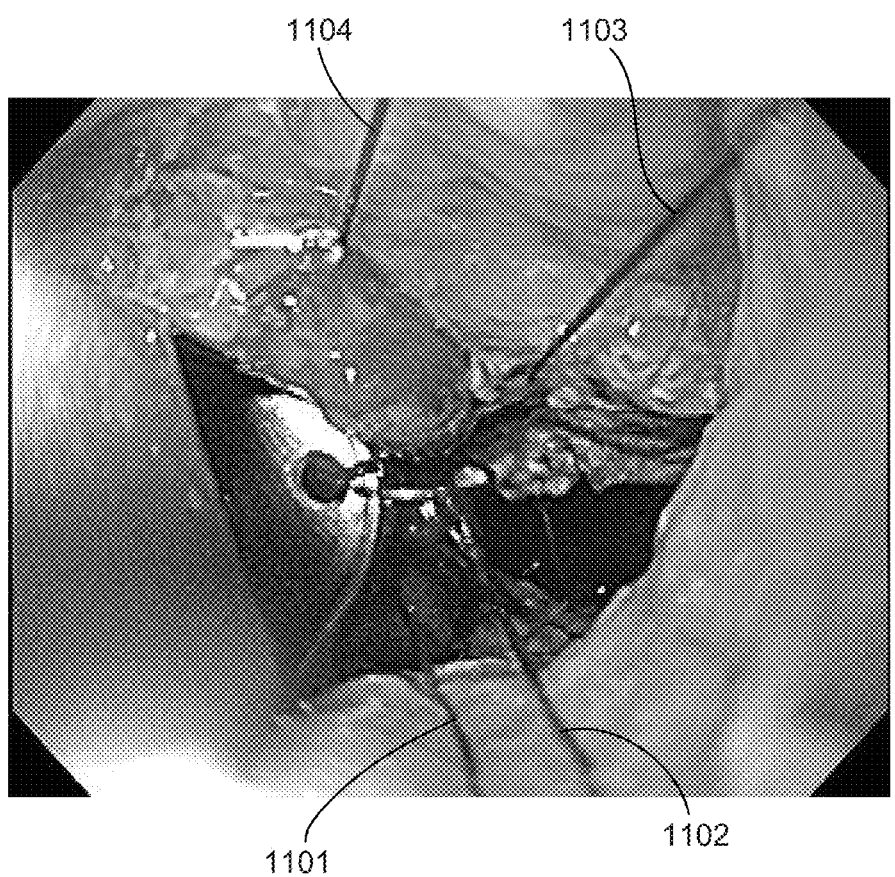

As shown in FIGS. 9A to 9D and 11, a C.R. Bard, Inc. EndoCinch® or other suturing device is used to aspirate tissue at the rim of the anastomosis and place a first stitch 1101. The device is then removed and reloaded. The cap is taken off retrieving the suture tag, the tag is then reloaded in the bevel of the needle, and the cap is replaced. The device is then re-introduced and a second stitch 1102 is placed adjacent to the first stitch. The suturing device is again removed and the sutures run out through the overtube and mouth and are held in place with a snap. This is then repeated until multiple stitches 1101-1104 are placed into the rim of the anastomosis as shown in FIGS. 11-13. The stitches are placed in an interrupted fashion and the second stitch is placed across from the first on the opposing part of the anastomotic rim instead of directly adjacent to the first stitch. Several stitches radiate out from the anastomosis, and it is important to keep these from becoming tangled.

Figure 14:
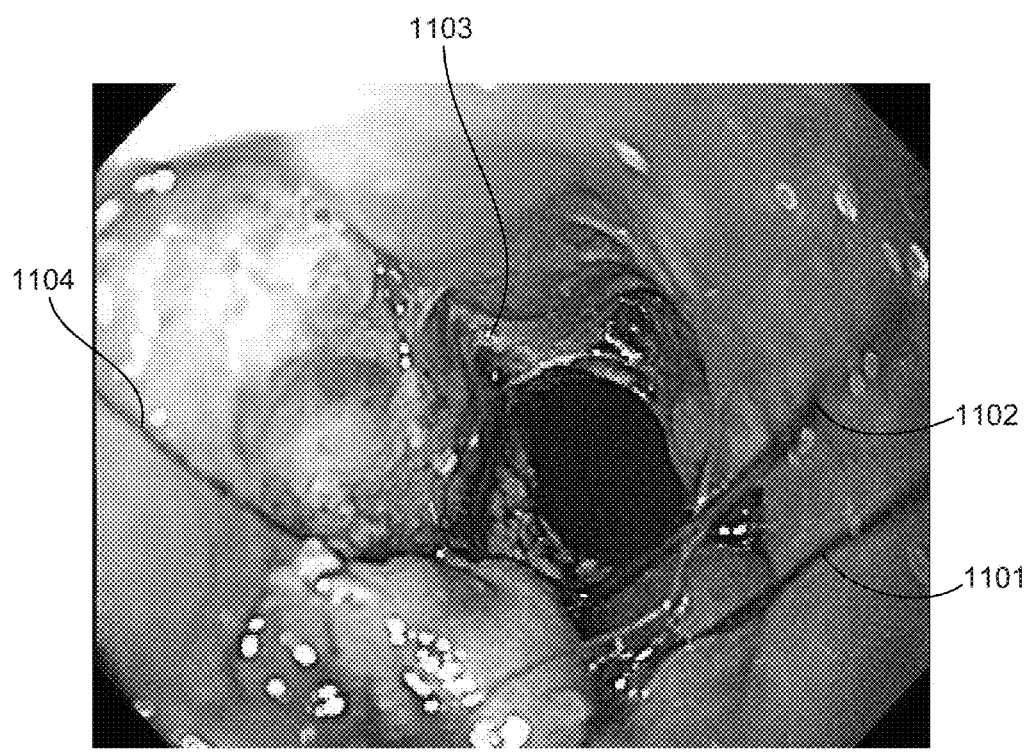
Figure 15:
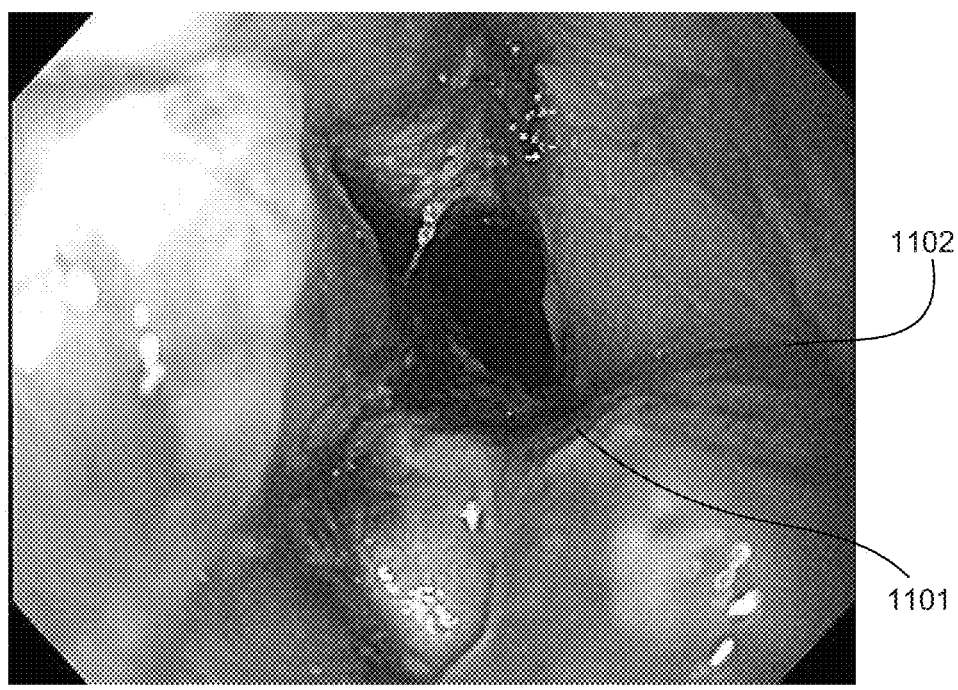
Figure 16:

Stitch pairing is confirmed and they are then tightened and secured using a cinching device (FIGS. 14 and 15). The excess suture material is simultaneously cut and removed. Ordinarily, these stitches are tied to form plications along the anastomosis, however, this limits how tight one can make the anastomosis, as the device must be re-introduced into a smaller and smaller opening. Finally, as shown in FIG. 16, we use a tissue sealant 32 such as Tisseel® or other type of fibrin glue or cyanoacrylate to protect the area and provide a fluid barrier. This is applied at the end of the procedure, e.g., with a double lumen biliary extraction balloon that has had the tip removed with scissors. Typically 2-5 ccs are applied. The result is an anastomosis that is much smaller compared to its original size.

The new methods use minimally invasive, endoscopic techniques for the repair of gastric bypass defects, such as the reduction of the gastrojejunal anastomosis, in patients with significant weight recidivism following RYGB. The new methods are technically feasible and safe, and provide a new treatment option to achieve renewed weight loss in certain patients with post-bypass weight regain.

EXAMPLES

The following examples are illustrative, and not limiting.

Example 1

Repairs of Intragastric Fistulas

A patient exhibited several gastric fistulas, which developed several months following Roux-en-Y gastric bypass surgery. In the Roux-en-Y procedure the patient's stomach had been partitioned through surgical stapling, and a resected portion of the patient's small intestine was then anastomosed to a newly created gastric pouch 50. FIG. 17A is an endoscopic photo as viewed looking down from the esophagus into the patient's surgically created gastric pouch 50. Four fistulas 52, 54, 56, and 58, are visible near the staple line dividing the larger defunctionalized stomach portion 60, and the smaller gastric pouch 50. The fistulas 52, 54, 56, and 58 are a result of staple line dehiscence, also referred to as suture line separation.

Figure 17B:
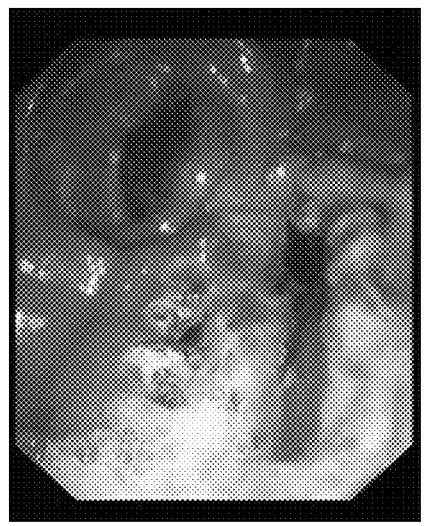
FIG. 17B is a representation of an endoscopic view of the gastric pouch and staple line of FIG. 17A after tissue surrounding several staple line fistulas has been burned to stimulate new tissue growth.

Referring to FIG. 17B, repair of the fistulas began by burning the surrounding tissue using argon plasma coagulation. This step was achieved using an APC catheter transorally delivered to the region of the fistula through the lumen of a flexible endoscope. The APC catheter was then removed from the endoscope and replaced with a conventional cytology brush, which was used to mechanical abrade and remove the burned and desiccated tissue.

Figure 17D:
FIG. 17D is a representation of a view of the gastric pouch after the staple line fistulas were closed using the endoscopic suturing technique.
Figure 17A:
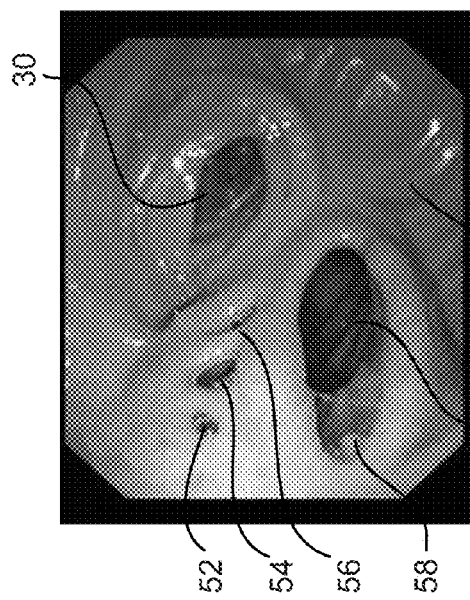
FIG. 17A is a representation of an endoscopic view of a gastric pouch and associated staple line formed in gastric bypass surgery.
Figure 17C:
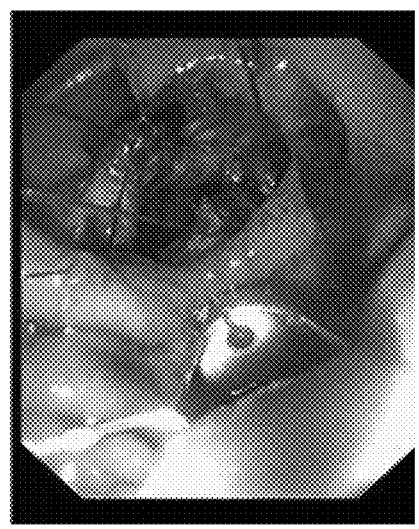
FIG. 17C is a representation of an endoscopic view of the gastric pouch and staple shown in FIG. 17B with burned tissue removed and interrupted sutures being endoscopically placed to close the staple line fistulas.

As shown in FIG. 17C, an EndoCinch® endoscopic tissue apposition and suturing device was delivered via a second flexible endoscope and used to place multiple, interrupted sutures transversely across the fistulas. FIG. 17D shows a gastric pouch after the staple line fistulas were closed using the endoscopic suturing technique. Thereafter, endoscopic clips were applied to reinforce the suture line. Finally, a double-lumen catheter was used to apply Tisseel® fibrin sealant to the suture line, encapsulating the endoscopic clips and suture line to facilitate tissue growth across the sutured fistula, repairing the defect.

Routine follow-up of the above-described and other similarly performed procedures demonstrates the foregoing technique is effective for repairing failed gastric bypass surgical procedures. Following dehiscence repair in accordance with the above-described technique, patients have exhibited weight loss in the range of forty to fifty pounds within four to five months following the procedure.

Example 2

Repairs of Dilated Gastrojejunal Anastomoses

Eight patients with significant weight regain and dilated gastrojejunal anastomosis after RNYGB were included in this study. In general, sutures were placed endoscopically at the rim of the anastomosis. When tightened, the sutures formed tissue plications reducing the size of the anastomotic aperture.

In particular, all patients had significant weight regain and underwent upper endoscopy to measure the size of their pouches as well as the aperture of the gastrojejunostomy. Other pouch or roux-limb pathology was ruled out. Only patients who were more than 2 years out after their RNYGB were eligible. Patients with significant psychiatric illness, gastro-gastric fistula, or other significant upper GI pathology were excluded.

All procedures were performed in the endoscopy unit using endotracheal anesthesia administered by a staff anesthesia team. Routine upper endoscopy was first completed to reevaluate the pouch and diameter of the anastomosis.

The mucosa was damaged prior to suturing to provide improved tissue healing so that the reduction is not dependent on the long-term presence of sutures. We ablated the mucosa of every patient using argon plasma coagulation. The argon provides more uniform and consistent depth of ablation. We also followed this ablation with mucosal stripping using a cytology brush to promote better tissue healing.

Figure 9A:
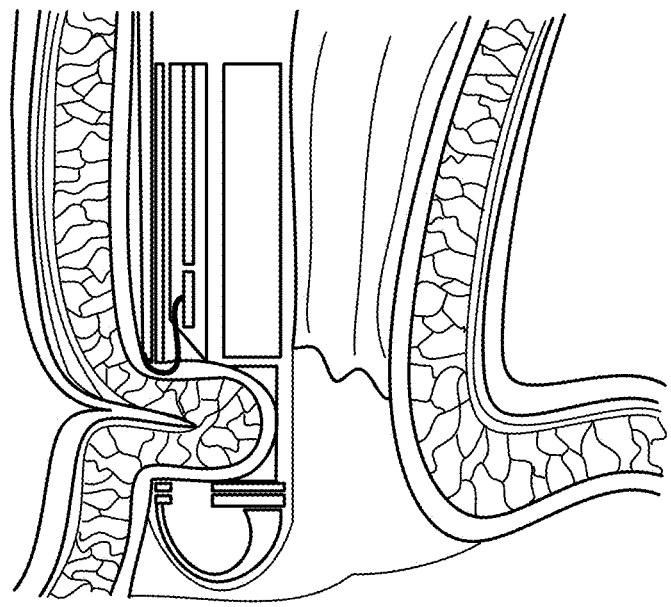
FIGS. 9A to 9D are a series of schematic representations of a dilated gastrojejunal anastomosis and steps in a repair that reduces the size of the opening.
Figure 9B:
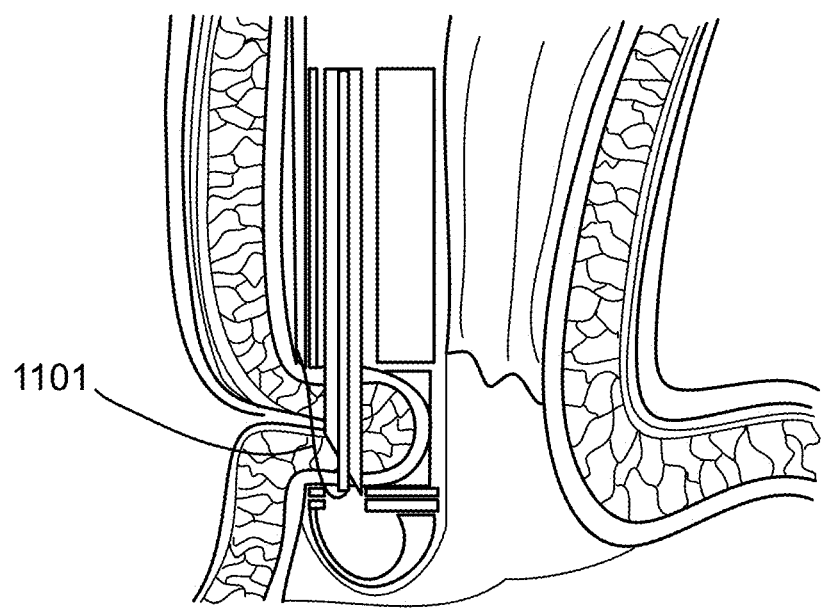
Figure 9C:
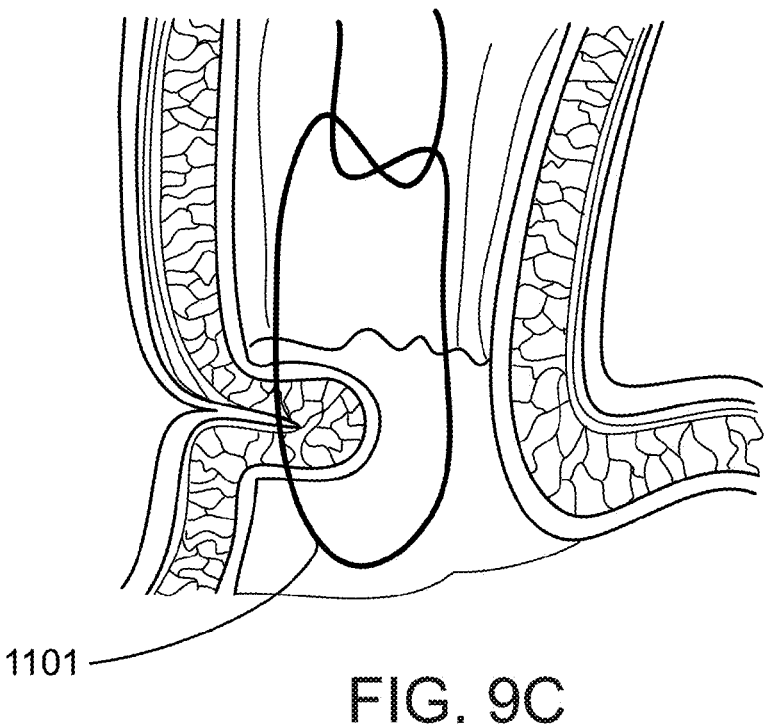
Figure 9D:
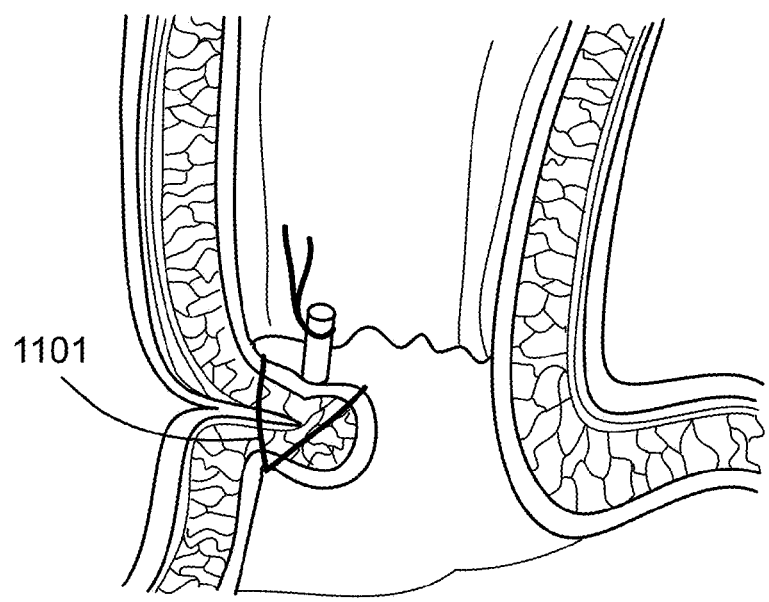
Figure 10:
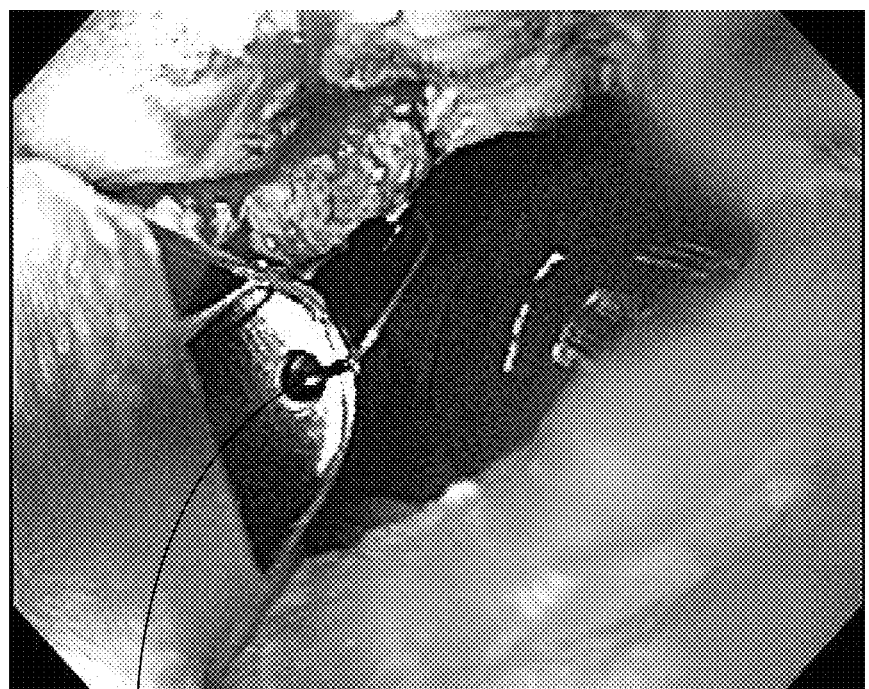
FIGS. 10-16 are a series of representations of endoscopic views of further steps in the repair of a dilated gastrojejunal anastomosis.

After the tissue was damaged and some of the tissue was removed, e.g., stripped, an EndoCinch® (C.R. Bard, Inc.) was then advanced through the GE junction to the gastrojejunostomy. As shown in FIG. 9A, tissue was aspirated into the capsule of the EndoCinch®, and FIG. 9B shows the needle being thrust through the tissue and the suture tag captured in the distal cap. As shown in FIG. 9C, the needle was then withdrawn, suction was discontinued, and the device was removed. The device was then reloaded and this step was repeated prior to forming a plication and securing the stitch as shown in FIG. 9D.

One to three interrupted stitches (depending on patient and size of the anastomosis) were placed around the rim of the gastrojejunostomy. After all stitches were placed, they were then tightened and secured forming tissue plications. The presence of these plications reduced the anastomotic aperture.

At the end of the procedure, we used a tissue sealant, Tisseel® fibrin glue, to protect and seal the area and provide a fluid barrier. Final anastomotic apertures were measured, and the pouch in each patient was carefully inspected to assess for complications. Patients were then awoken from general anesthesia and monitored in the endoscopy unit recovery room. All patients were discharged to home that day with instructions regarding concerning symptoms, follow-up, and diet. Patients were placed on a full liquid diet for three days and then soft solids for one week.

For follow-up patients were seen at one and four months post-procedure. They were weighed on the same digital scale and asked about post-procedure symptoms, diet, eating habits, activity, and satiety levels. Repeat procedures were performed in three patients.

A total of 8 subjects were included in this study. All subjects were female with a mean age of 46 years (41-54 years). Average time since bypass was 6 years (1-22 years) with a mean maximal weight loss of 49 kg (40-68 kg). Weight regain was the primary indication for the endoscopic anastomotic reduction and patients had regained an average of 24 kg (8.6-53.6 kg) from their post RNYGB nadir. At initial upper endoscopy, the mean pouch length and anastomosis diameter were 5.7 cm (3-8 cm) and 25 mm (17-25 cm), respectively. Three patients had small sliding hiatus hernias and one patient had a dilated pouch on UGI series. Two patients had a distant history of gastrojejunal anastomotic stenosis treated with endoscopic dilatation.

During the procedure, an average of two interrupted stitches were placed (1-3 stitches). At the end of the procedure the mean anastomosis diameter was 10 mm (5-15 mm), which yielded an average reduction of 15.5 mm (62% reduction). Mean procedure length was 98 minutes (50-164 minutes).

Figure 18A:
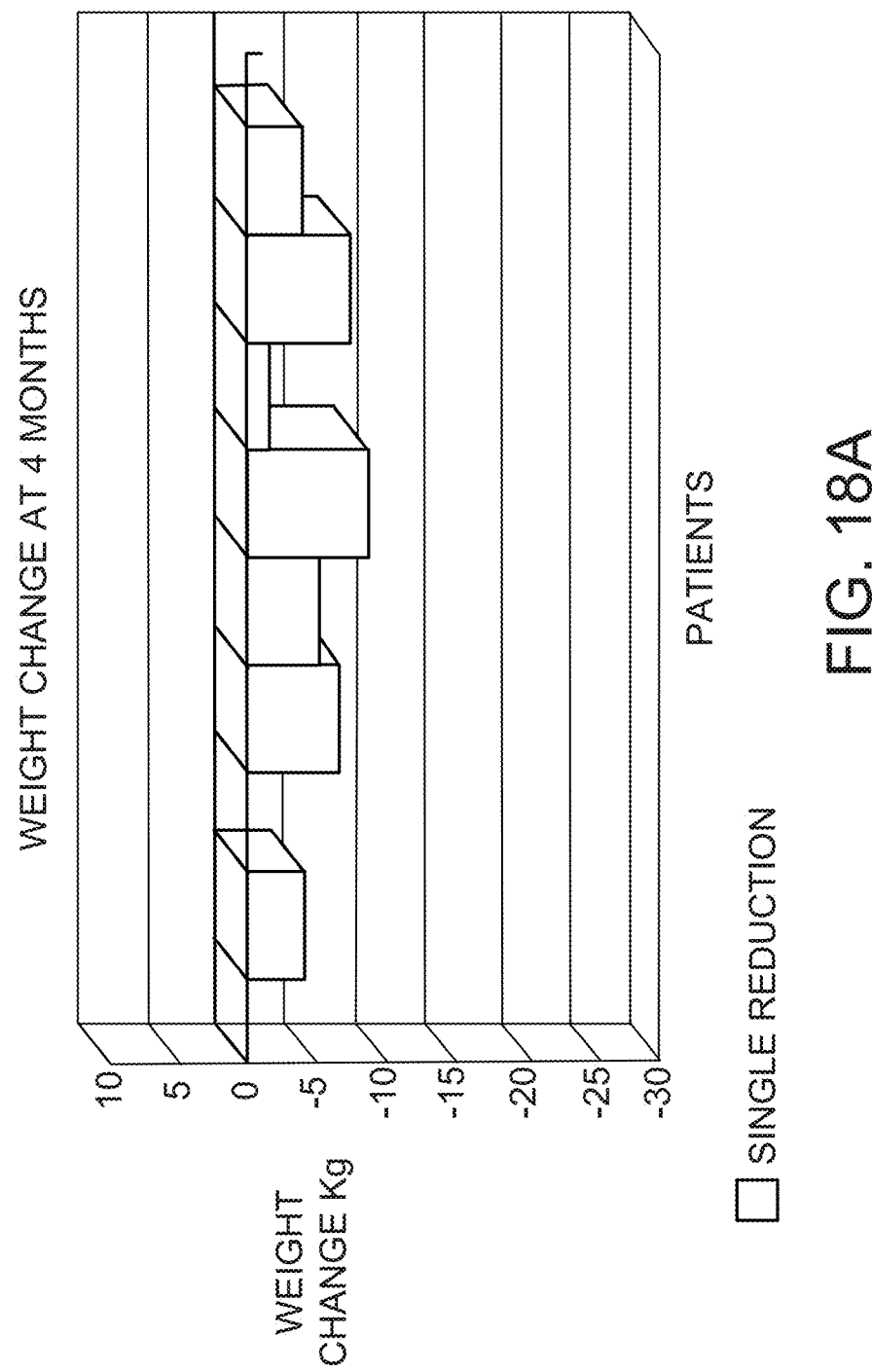
FIGS. 18A and 18B are a pair of graphs showing weight change in eight individual gastric bypass repair patients at 4 and 5 months, respectively.

As shown in FIG. 18A, at a mean follow-up of 4 months, 6 of 8 patients had lost weight, with an average weight loss among these 6 patients of 10 kg (1.4-19.5 kg). The Y-axis is change in weight and the X-axis is patients 1 through 8. Four patients reported significant improvement in satiety. Three subjects reported brief improvement in satiety and requested repeat procedures; these subjects lost 4, 5, and 9 kg, respectively. The patient with the dilated pouch on UGI reported no improvement in satiety and lost 3.6 kg.

Figure 18B:
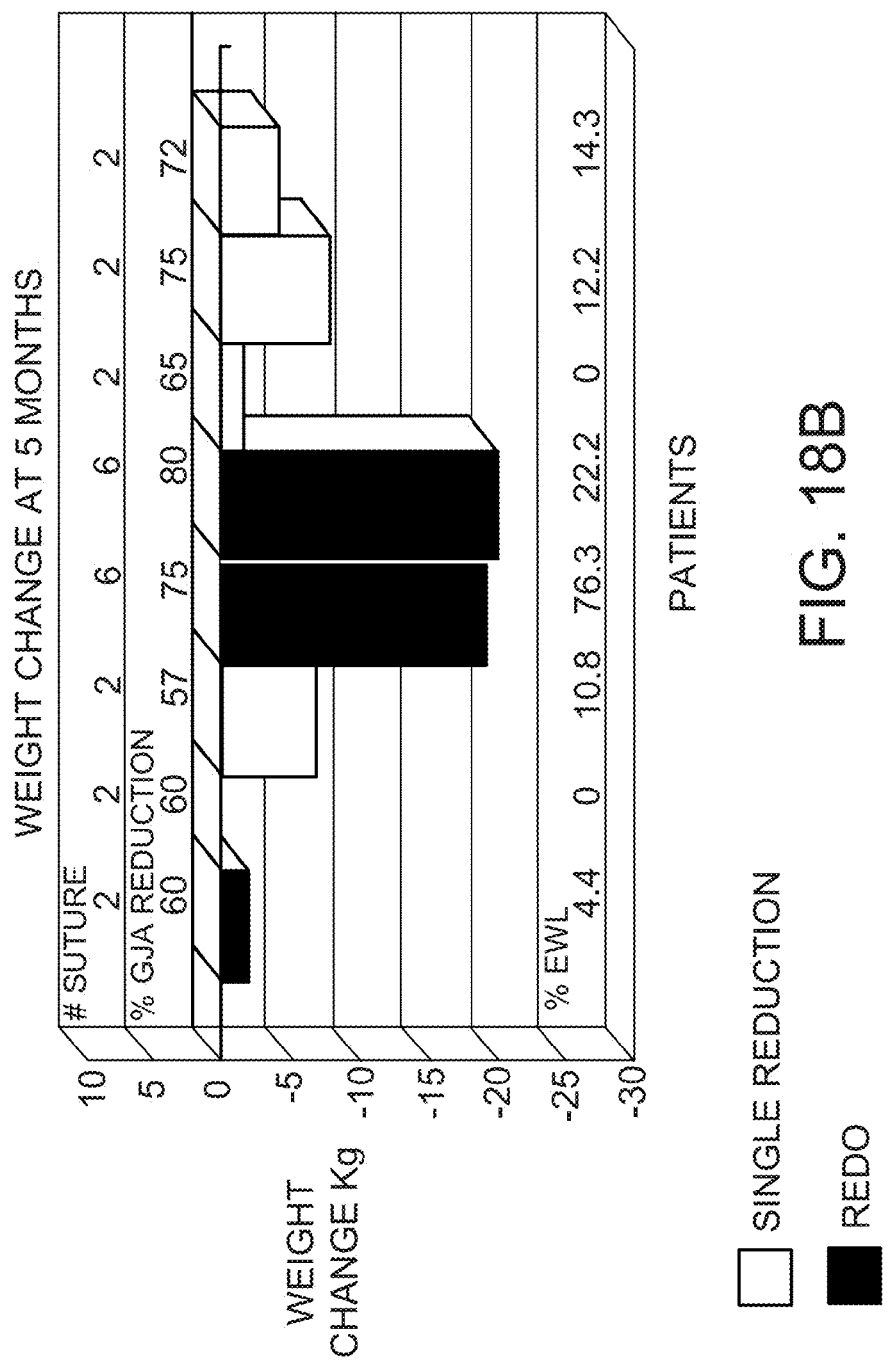

The 3 subjects with temporary improvement in satiety and normal pouch size underwent a second anastomotic reduction using the EndoCinch® device with final diameters of 14, 5, and 5 mm, respectively. As shown in FIG. 18B, the first patient did not experience further weight loss. The remaining two lost a total of 19 and 20 kg at 5 months. Of the three patients with gastroesophageal reflux disease-like (GERD-like) symptoms prior to the procedure, two reported resolution of symptoms.

The two patients who did not lose weight each reported improved satiety at the one-month follow-up visit, but not at subsequent visits. One of the patients did not gain further weight while the other patient gained 1.4 kg at one-month and was then lost to follow-up. Each patient had anastomotic starting diameters of 2 cm and had two interrupted stitches placed during the procedure with final diameters of 7 and 8 mm. The first patient reported eating large amounts of soft, solid, high caloric foods and the second reported significant emesis for a few days following the procedure.

All 11 reductions (8 initial, 3 secondary) were performed without significant immediate or delayed complications. Following the procedure two patients reported post procedural emesis lasting a few days and one patient described epigastric discomfort lasting a few days. Symptomatic complaints from the procedure were self-limited and included a transient sore throat, abdominal discomfort, and nausea.

Based on the results to date, the new methods described herein provide a useful treatment option for weight regain in selected patients after RNYGB. Endoscopic anastomotic reduction is feasible and safe, and is associated with variable weight loss.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of perorally repairing a defect occurring after gastric bypass surgery in a patient with post-gastric bypass weight regain or a failure to achieve a sustained weight loss, wherein the defect comprises a fistula located between the patient's gastric pouch and a defunctionalized portion of the stomach or a dilated gastrojejunal anastomosis, the method comprising
    damaging tissue portions adjacent to the defect;
    removing at least some of the damaged tissue portions;
    perorally advancing a suturing device into the patient adjacent to the defect;
    gathering a first fold of tissue along a rim of the defect;

operating the suturing device to advance a suture material, staple, or clip through the first fold of tissue;

gathering a second fold of tissue along the rim of the defect, adjacent to the first fold of tissue;

operating the suture device to advance a suture material, staple, or clip through the second fold of tissue; and bringing together the first and second folds of tissue to at least partially reduce the defect to decrease the passage of food through the defect.

2. The method of claim 1, wherein the suture material is tightened with a cinching device.

3. The method of claim 1, further comprising applying a sealant to cover the suture material.

4. The method of claim 1, wherein two, three, or more folds of tissue are brought together.

5. The method of claim 1, wherein the tissue is thermally damaged.

6. The method of claim 1, wherein the tissue is thermally damaged with a heat probe or by argon plasma coagulation.

7. The method of claim 1, wherein the suture material comprises a single strand of material.

8. The method of claim 1, wherein the suture material comprises two or more individual strands of material.

9. The method of claim 1, wherein damaged tissue is removed by mechanical abrasion.

10. The method of claim 1, wherein the defect is a dilated gastrojejunal anastomosis.

11. The method of claim 1, wherein the defect is a fistula resulting from staple line dehiscence.

12. The method of claim 1, further comprising applying a reinforcing clip to the first and second folds of tissue.

13. The method of claim 12, wherein the reinforcing clip is a hemostatic clip.

14. The method of claim 1, further comprising applying a sealant to cover the suture material, staple, or clip and/or clip.

* * * * *

UNITED STATES PATENT AND TRADEMARK OFFICE
CERTIFICATE OF CORRECTION

PATENT NO. : 8,623,009 B2  
APPLICATION NO. : 11/909728  
DATED : January 7, 2014  
INVENTOR(S) : Christopher C. Thompson It is certified that error appears in the above-identified patent and that said Letters Patent is hereby corrected as shown below:

In the Claims

In Column 11, line 17, Claim 6, delete "claim 1," and insert -- claim 5, --

Signed and Sealed this
Fifteenth Day of July, 2014

Michelle K. Lee
*Deputy Director of the United States Patent and Trademark Office*